United States Patent
Alpenfels et al.

(10) Patent No.: US 7,033,477 B2
(45) Date of Patent: Apr. 25, 2006

(54) ELECTROPHORESIS GEL ASSEMBLY

(75) Inventors: William F. Alpenfels, Del Mar, CA (US); Marilyn Alpenfels, Del Mar, CA (US)

(73) Assignee: Grace Ventures LLC, Del Mar, CA (US)

( * ) Notice: Subject to any disclaimer, the term of this patent is extended or adjusted under 35 U.S.C. 154(b) by 467 days.

(21) Appl. No.: 10/306,754

(22) Filed: Nov. 27, 2002

(65) Prior Publication Data

US 2003/0141190 A1  Jul. 31, 2003

Related U.S. Application Data

(60) Provisional application No. 60/335,231, filed on Nov. 30, 2001.

(51) Int. Cl.
*G01N 27/453* (2006.01)

(52) U.S. Cl. .................................... 204/616; 204/466
(58) Field of Classification Search ................ 204/606, 204/616, 618, 456, 466, 467
See application file for complete search history.

(56) References Cited

U.S. PATENT DOCUMENTS

| | | | |
|---|---|---|---|
| 4,101,401 A | 7/1978 | Hoefer | |
| 4,385,974 A | 5/1983 | Shevitz | |
| 4,715,942 A | 12/1987 | Tezuka et al. | |
| 4,773,984 A | 9/1988 | Flesher et al. | |
| 4,820,398 A | 4/1989 | Yamamoto | |
| 4,865,715 A | 9/1989 | Hellman, Jr. | |
| 4,867,855 A | 9/1989 | Burton | |
| 5,104,512 A | 4/1992 | Gombocz et al. | |
| 5,217,591 A | 6/1993 | Gombocz et al. | |
| 5,753,095 A * | 5/1998 | Alpenfels et al. | 204/616 |

* cited by examiner

*Primary Examiner*—Kaj K. Olsen
(74) *Attorney, Agent, or Firm*—Stephen C. Beuerle; Procopio, Cory, Hargreaves & Savitch LLP (57) ABSTRACT

A thin-film electrophoresis assembly includes a support frame having a top portion and a substantially flat face, a first thin-film member carried by the support frame, a second thin-film member carried by the support frame, and a resolving gel sandwiched between the first thin-film member and the second thin-film member. A reservoir is mounted to the top portion of the support frame and includes an open top and an open bottom. A stacking gel is carried by the reservoir and includes a bottom surface in fluid-tight communication with a top surface of the resolving gel through the open bottom of the reservoir.

10 Claims, 8 Drawing Sheets

ELECTROPHORESIS GEL ASSEMBLY

Applicants claim the benefits of U.S. Provisional Patent Application entitled Electrophoresis Gel System, Patent Application No. 60/335,231, filed by the named inventors on Nov. 30, 2001. Said provisional patent application is incorporated herein by reference.

FIELD OF THE INVENTION

The invention relates to electrophoresis gel assemblies and methods of assembling electrophoresis gel assemblies.

BACKGROUND OF THE INVENTION

Electrophoresis for the separation of biological molecules such as DNA, RNA, polypeptides, polynucleotides, polysaccharides, and proteins has been performed for many years. An electrophoresis gel assembly may include running buffers at opposite ends of the gel assembly. The gel may include a non-convective separating medium in an aqueous buffer contained in an enclosure or cassette. The opposite ends of the gel assembly are generally exposed to the running buffers. Electrodes are placed in the buffers at each end of the gel assembly with an electrical potential applied to the electrodes to impose an electric field, which is passed through the gel. The samples to be analyzed are typically located at one end of the gel. When the electrical charge is applied, the sample molecules migrate towards one electrode through the gel in a manner that is dependent on the potential associated their charge and physical size.

Two major types of electrophoretic separations are used: One-dimensional ("1D") and two-dimensional ("2D") electrophoresis. In 1D electrophoresis, either a tube or slab gel assembly is made; separations are usually by one of two mechanisms: size or charge. Other properties may be exploited as well.

Size separations is the most common mechanism employed in 1D electrophoresis. Such separations are based on differential rates of migration of the macromolecules, such as proteins or polynucleotides, through the gel matrix, where the rate of migration is dependent on two factors: charge density of the macromolecules and migration restriction. For all size separation cases, the restriction factor is a function of molecular size (affected by molecular weight and shape) and the matrix polymer concentration. Many elements influence charge density and shape in size separations. In native protein size separations, the charge density is dependent on the amino acid composition and the pH of the buffers employed, and the shape varies considerably from protein to protein. In denaturing protein size separations, a denaturant, generally a charged detergent, and usually a reducing agent is used to disrupt the secondary and tertiary protein structure forming more or less similar shape macromolecules; when the denaturant is charged, the proteins tend to have a uniform charge density, as well. In polynucleotide size separations, the charge density and shape is usually uniform whether or not denaturants are employed. When both the charge density and the shape are uniform, the separation in a given matrix polymer concentration is solely dependent on molecular weight.

Electrophoresis gels were originally made from starch or cellulose. However, agarose and cross-linked polyacrylamide (Raymond and Weintraub 1959) are widely used as the main gel materials today. Agarose is particularly useful for large double-stranded DNA ("ds-DNA") separations. Poly acrylamide gel electrophoresis ("PAGE") is used for higher resolution separations of somewhat smaller bio-molecules. A cross-linked polyacrylamide gel ("PAG") is formed by polymerizing acrylamide monomer together with a cross-linker, usually N,N'-methylene-bis-acrylamide ("Bis"). Various derivatives of these materials have been used to enhance the performance and stability of the gel. The concentration of gel material can be varied over a broad concentration range to change its behavior. With high concentrations of gel material (such as 20% acrylamide), small molecules can be separated. Lower concentration gel materials (such as 8% acrylamide) are useful for larger molecules. A gradient of low to high acrylamide and/or Bis concentrations, formed either continuously or step-wise, produces a single gel able to separate a broad range of sizes such as in a 4–20% acrylamide gel.

Traditionally in 1D size separations, the same buffer was employed in the solutions at each end of the gel assembly (known as cathode and anode running buffers) and in the gel itself. This technique was known as zone electrophoresis, since the molecules are separated into distinct zones or bands. Currently, zone electrophoresis system is more frequently known as a continuous buffer system, which is widely used with Tris/borate/EDTA ("TBE") buffer solutions for ds-DNA separations. When denaturants, such as urea or formamide, are added to the gel and sample, this same system is useful for separating single-stranded RNA or DNA, especially in DNA sequencing applications.

In 1964, Ornstein and Davis described a discontinuous gel system for 1D protein size separations. They used a Tris/chloride buffer at pH 6.8 in a low percentage—typically 4% PAG—first gel, also known as a stacking gel, on top of a second, higher percentage gel—typically in the range of 8 to 20% PAG, as a single percentage or a gradient from low to high monomer concentration—containing Tris/chloride buffer at pH 8.8, also known as a separating gel. The combination of these gels forms a gel system that is used in conjunction with a Tris/glycine running buffer. The Ornstein/Davis gel and buffer system, in conjunction with a gel enclosure, produces a Multiphasic Zone Electrophoresis assembly, since different buffer species are present in the gel assembly at different times. Protein samples are introduced to this assembly, and the gel assembly is run in a vertical position. During the initial part of the separation, distinct chemical phases appear. The leading phase in the gel comprises chloride ions (also known as the leading ion). It migrates faster than the trailing phase comprising negatively charged glycine ions (also known as the trailing ion). In between these two phases is the stacking phase. Since the pH of the trailing phase is about 9.7 and the pH of the leading phase is 8.8, an inverse pH gradient is created. When protein mixtures are introduced as a broad band, the leading edge of the band at a lower pH travels slower than the trailing edge at a higher pH. This phenomenon causes the proteins to stack into a sharp band between the leading and trailing phases. When the stacked proteins reach the higher percentage separating gel, the proteins are restricted by the higher polymer concentration in the gel matrix and migrate slower than the ions; the proteins thereby escape from the stacking phase. The proteins then migrate at different rates depending on their size and charge density. Such discontinuous or "stacking" assemblies can be applied to other macromolecules as well.

Laemmli in 1970 modified this assembly further to include an anionic detergent, sodium dodecyl-sulfate ("SDS") that coats proteins to produce a uniform charge density on them. When cysteine-cysteine disulphide bonds are reduced, the proteins are separated primarily on the basis of size. These improvements have made SDS-PAGE one of the most popular and simple techniques used in biological and life sciences research. Concurrently, in 1973, Jovin published a theory and criteria for selecting among some 6,000 chemical combinations for selecting an appropriate buffer assembly for producing Multiphasic Zone Electrophoresis.

Another major mechanism employed in 1D separations is charge. The most common technique utilizing this mechanism (e.g., see Chrambach et al., U.S. Pat. No. 4,139,440) is isoelectric focusing ("IEF"), where the gel buffer is replaced with low concentrations of multiple low molecular weights, amphoteric compounds. ("Ampholines"). These Ampholines are characterized by having functional groups with a different $pK_a$ exhibiting zero net charge at a specific pH, but negative or positive charge at a different pH value. Then, with an acid and a base as the anode and cathode buffers, the gel assembly is subjected to an electric field, and the Ampholines will distribute themselves to form a pH gradient. If a protein., or other amphoteric macromolecule, is added to the gel (before or after the pH gradient is formed), the individual molecule units of the macromolecules will migrate either towards the anode or cathode depending on net charge of the macromolecule until such molecules reach a point in the pH gradient where it has no net charge (known as its isoelectric point, or pI). Thus separation occurs by net charge on the protein independent of size or shape. A variation on this technique uses a pre-formed gradient of a fewer number of Ampholines that co-polymerize in the gel forming an immobilized pH gradient ("IPG").

Further improvements to resolving abilities have been made through 2D electrophoresis. When a sample is separated using IEF or IPG methods, then that gel is subjected to SDS-PAGE transverse to the original direction, a two-dimensional separation is achieved: first by charge then by size (e.g., Hochstrasser, U.S. Pat. No. 4,874,490). Other examples used non-denaturing first dimensions, and denaturing second dimensions to achieve separation first by native conformational size, then by absolute size. These two-dimensional methods are capable of resolving thousands of components from a single sample.

Other improvements have appeared in buffer assemblies recently. A discontinuous neutral pH assembly using Bis-Tris/chloride gels with TES (N-tris(hydroxymethyl)-2-ethane-sulfonic acid) was first described by Jovin in 1973 and demonstrated by Moos in 1988 using BisTris/chloride gels. An adaptation of this assembly is also described (Engelhorn et al., U.S. Pat. No. 5,578,180), where a different cation (Tris) is used in the anode buffer than in the gel. These neutral pH assemblies are reported to extend the shelf life, increase run speed through stability to higher temperatures caused by the higher electric-field strengths, and reduce protein modifications during electrophoresis. A continuous neutral pH buffer assembly for DNA and RNA separations has been described as well (Updyke, et al., U.S. Pat. No. 5,922,185). These latter two gels are sold under the trade names of NuPAGE® and QuickPoint®, respectively. A discontinuous buffer assembly for DNA separations has also been published (Zsolnai, et al., 1993).

To perform electrophoresis, a suitable gel assembly is needed with buffer solutions that are held in contact with each end of the gel. When performing Multiphasic Zone Electrophoresis, the different buffers must be held in separate chambers. Typically, the gel is encased in a glass or plastic tube, or between glass or plastic plates to form a slab gel. Sometimes gels are cast on a thin piece of plastic film, with or without a covering layer. Such film gel assemblies may be run with or without supporting plates or frames.

Various chambers have been used to hold the buffer solution and the gel assembly, and to provide contact for the electric potential. For example, a simple assembly for continuous buffer applications uses a submarine chamber. In such a device, samples are loaded into wells or depressions formed on the surface of an open-faced gel—typically agarose cast on a plate or film—which is horizontally disposed and submerged in the buffer with a charged applied at each end of the chamber.

Other horizontal electrophoresis chambers use wicks to draw buffer from side wells with the electrodes to the surface at each end of the gel assembly. These chambers also typically use homogeneous gels and are employed when the cathode and anode buffers must be kept apart, such as in isoelectric focusing (IEF). A significant draw back of horizontal electrophoresis gel assemblies is that the effect of differential temperature is amplified on both molecular migration rates and pH gradients. When placed in a horizontal position, the upper surface of the gel is typically hotter than the lower. Such temperature differences results in different migration rates or pH gradients through the thickness of the gel, which causes sloping bands across that variation. When looking at bands through one surface, the separation is likely to appear to have lower resolution due to wider bands.

Better chambers run gel assemblies vertically. When heat is dissipated equally out of both large surfaces of a slab gel assembly, the separation tends to have higher resolution. The vertical gel assemblies are also easier to load samples into wells formed in the top of the gel. These gels are harder to cast and the gel assembly harder to seal in the chamber. One chamber uses a cam to seal the gel assembly to a buffer core (Levy, U.S. Pat. No. 6,001,233). Another product first sold by PhorTrans (Mountain View, Calif.) in the late 1980's then later by Amersham in the early 90's used an upper buffer chamber molded into the cassette, which solved the sealing problem. The Criterion System from Bio-Rad (Hercules, Calif.) uses a similar approach. A wedge-shaped profile was also devised for ease of sample loading in very thin gels (Chu, et al., U.S. Pat. No. 5,284,565). The common characteristic of all gel assemblies that run vertically is that they must be in some sort of sealed cassette. The challenge has been to build a gel cassette that seals well, can be filled easily and reproducibly, can be sealed in a chamber for the electrophoresis run, and remains easy to open after the run is complete for further processing steps (such as staining or transfer).

A number of devices are used for forming electrophoresis gel assemblies. Glass plates with spacers are the traditional choice, and are employed by most people who pour the gels themselves (for example, Perez, et al., U.S. Pat. No. 6,162, 342). Commercial gel assemblies tend to be made from plastic plates (NOVEX gel, Invitrogen Corp., Carlsbad, Calif.; Margolis, U.S. Pat. No. 5,288,465; Lebacq, U.S. Pat. No. 5,407,552; Haven et al., U.S. Pat. No. 5,827,418; and Van Atta, U.S. Pat. No. 6,093,301), a combination of glass and plastic plates (Kushner, U.S. Pat. No. 4,954,236), or on plastic film (the Phast™ System, Pharmacia Piscataway, N.J.; Sugimoto, U.S. Pat. No. 4,897,306; Ogawa, U.S. Pat. No. 4,737,259; and Alpenfels, et al., U.S. Pat. No. 5,753, 095). These commercial devices are employed to reduce costs of production and fall into two general types:

(a) A rigid glass or plastic mold sealed on four or five sides where each gel is formed individually and consist of homogeneous gels, homogeneous separating gels with a stacking gel, or concentration gradient gels; and (b) plastic-film-backed homogeneous gels poured in large slabs or continuously.

The former devices make it easier to form monomer concentration variations such as a stacking gel or gradient gels and possible to seal the gel assembly in a chamber for running vertically, but are more expensive and complicated to manufacture. Sometimes a film support layer, generally with an adhesive coating, is used inside the mold when the gel is cast, so that the gel will be bound to the film for subsequent processing steps; this bonded-gel assembly maintains gel integrity during processing steps, and is particularly important for thin gels (0.5 mm or less in thickness). The latter devices are less expensive to produce and can contain an adhesive layer as a normal component, but lack the flexibility and performance of the former, especially in regards to monomer concentration changes for a stacking gel or gradient gel. These latter devices also have other deficiencies: they have no stacking gel, are run horizontally producing lower resolution, require a complicated carrier assembly to run vertically (see Tezuka, et al., U.S. Pat. No. 4,715,942 and Yamamoto, et al., U.S. Pat. No. 4,915,811) or may be difficult to load. Processes have been patented to produce thickness or concentration gradient gels horizontally on plastic film (Sugihara, et al., U.S. Pat. No. 4,834,854 and Sugihara, et al., U.S. Pat. No. 5,190,629), but neither of these methods has enjoyed any commercial success. However, even when a stacking and separating gel are included, the gels are always in contact with one another and must either be used immediately or have identical diffusible compound composition and concentration. Furthermore, there is no opportunity to have a 2D electrophoresis gel assembly in the above configurations as the different chemical components of those techniques would similarly diffuse.

Some inventions have tried to circumvent the loading and buffer sealing problems of horizontal gel assemblies. In the Phast System, comb-like pieces of filter paper are used to hold samples, and this sample "wick" is placed between the separating gel and a buffer block. This system has only been used commercially for very small gels run horizontally, with limited sample capacity and resolution. Another approach (Rice, et al., U.S. Pat. No. 5,972,188) uses a comb-shaped nitrocellulose membrane. Samples are loaded onto it, the membrane is inserted into the gel assembly, and the system is run horizontally. This approach also has resolution problems and no stacking gel.

SUMMARY OF THE INVENTION

An aspect of the invention involves a thin-film electrophoresis assembly including a support frame having a top portion and a substantially flat face, a first thin-film member carried by the support frame, a second thin-film member carried by the support frame, and a resolving gel sandwiched between the first thin-film member and the second thin-film member. A reservoir is mounted to the top portion of the support frame and includes an open top and an open bottom. A stacking gel is carried by the reservoir and includes a bottom surface in fluid-tight communication with a top surface of the resolving gel through the open bottom of the reservoir.

Another aspect of the invention involves a support frame for an electrophoresis assembly including a first thin-film member, a second thin-film member, an electrophoresis gel there between, and a reservoir including front and rear protruding members that extend outward and laterally from the reservoir. The support frame includes a substantially rectangular support frame having an interconnected upper lateral support, a lower lateral support, a left vertical support, a right vertical support, and ear-like, flat protrusions that extend from the support frame near intersections of the interconnected upper lateral support with the vertical supports. The ear-like, flat protrusions are slidably received by the front and rear protruding members to mount the reservoir on top of the support frame.

A further aspect of the invention involves a reservoir for an electrophoresis assembly including a support frame that carries an electrophoresis gel sandwiched between a first thin-film member and a second thin-film member, the support frame including ear-like, flat protrusions that extend upwardly from a top portion of the support frame. The reservoir includes a trough-shaped member including an open top and an open bottom. The reservoir decreases in thickness from the open top to the open bottom. Front and rear protruding members extend outward and laterally from the reservoir and slidably receive the ear-like, flat protrusions of the support frame to mount the reservoir on top of the support frame.

Another aspect of the invention involves a method of assembling an electrophoresis assembly. The method includes providing a substantially rectangular support frame having an interconnected upper lateral support, a lower lateral support, a left vertical support, a right vertical support, and ear-like, flat protrusions that extend from the support frame near intersections of the interconnected upper lateral support with the vertical supports, the support frame carrying an electrophoresis gel sandwiched between a first thin-film member and a second thin-film member; providing a reservoir including a trough-shaped member including an open top and an open bottom, the reservoir decreasing in thickness from the open top to the open bottom, front and rear protruding members extending outward and laterally from the reservoir, and mounting the reservoir to the support frame by sliding the front and rear protruding members of the reservoir over the ear-like, flat protrusions of the support frame.

A still further aspect of the invention involves a method of assembling an electrophoresis assembly. The method includes separately casting a stacking gel and a resolving gel; providing the stacking gel in a reservoir having an open bottom; providing the resolving gel between two thin-film members on a support frame, the resolving gel having a top edge and a perimeter that is not sealed; and joining the stacking gel with the top edge of the resolving gel through the open bottom of the reservoir.

Further objects and advantages will be apparent to those skilled in the art after a review of the drawings and the detailed description of the preferred embodiments set 5 forth below.

DETAILED DESCRIPTION OF PREFERRED EMBODIMENTS

Figure 1:
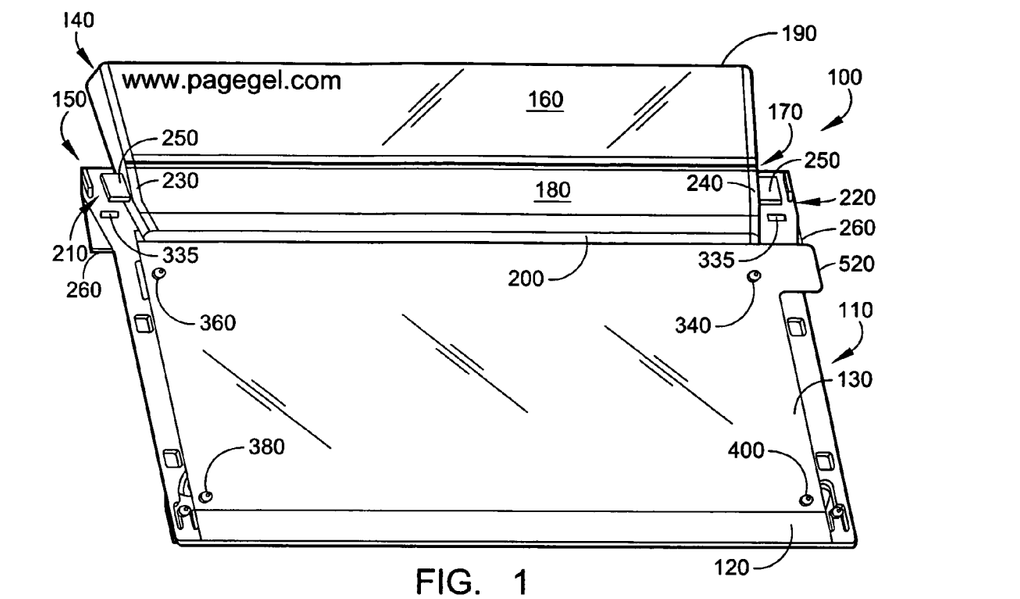
FIG. 1 is a perspective view of an embodiment of a thin, plastic-film gel electrophoresis assembly.

With reference to FIG. 1, a thin, plastic-film gel electrophoresis assembly 100 constructed in accordance with an embodiment of the invention will now be described. The assembly 100 includes a support frame 110 that carries a separating or resolving gel 115 (FIG. 2) sandwiched between a first, inner thin-film member 120 and a second, outer thin-film member 130. A reservoir 140 is mounted to a top 150 of the support frame 110.

Figure 2:
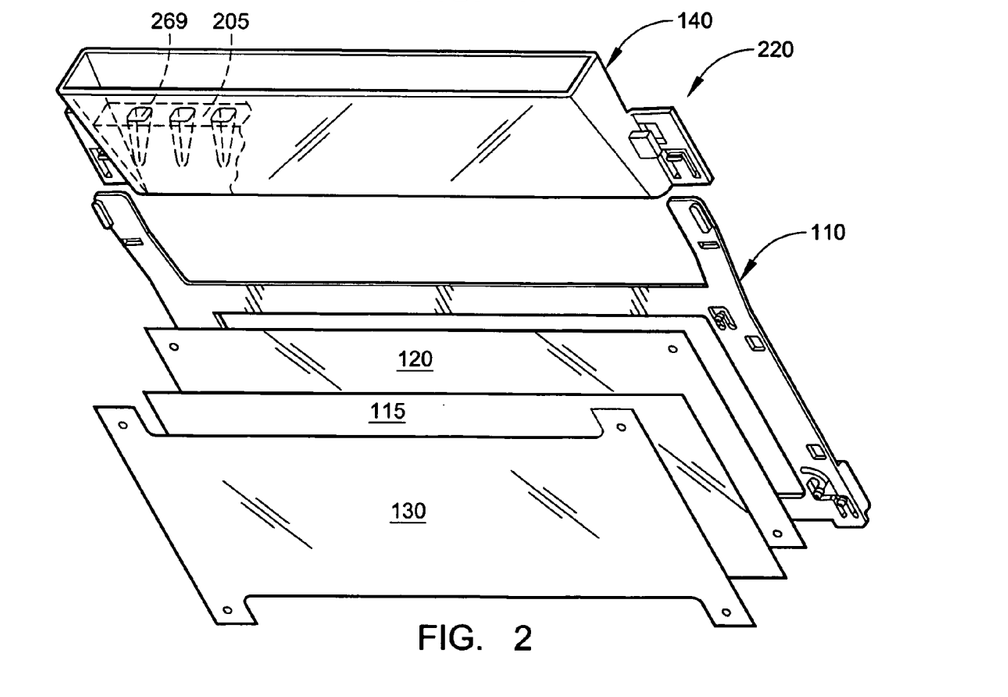
FIG. 2 is an exploded perspective view of the thin, plastic-film gel electrophoresis assembly illustrated in FIG. 1.
Figures 3A, 3B:
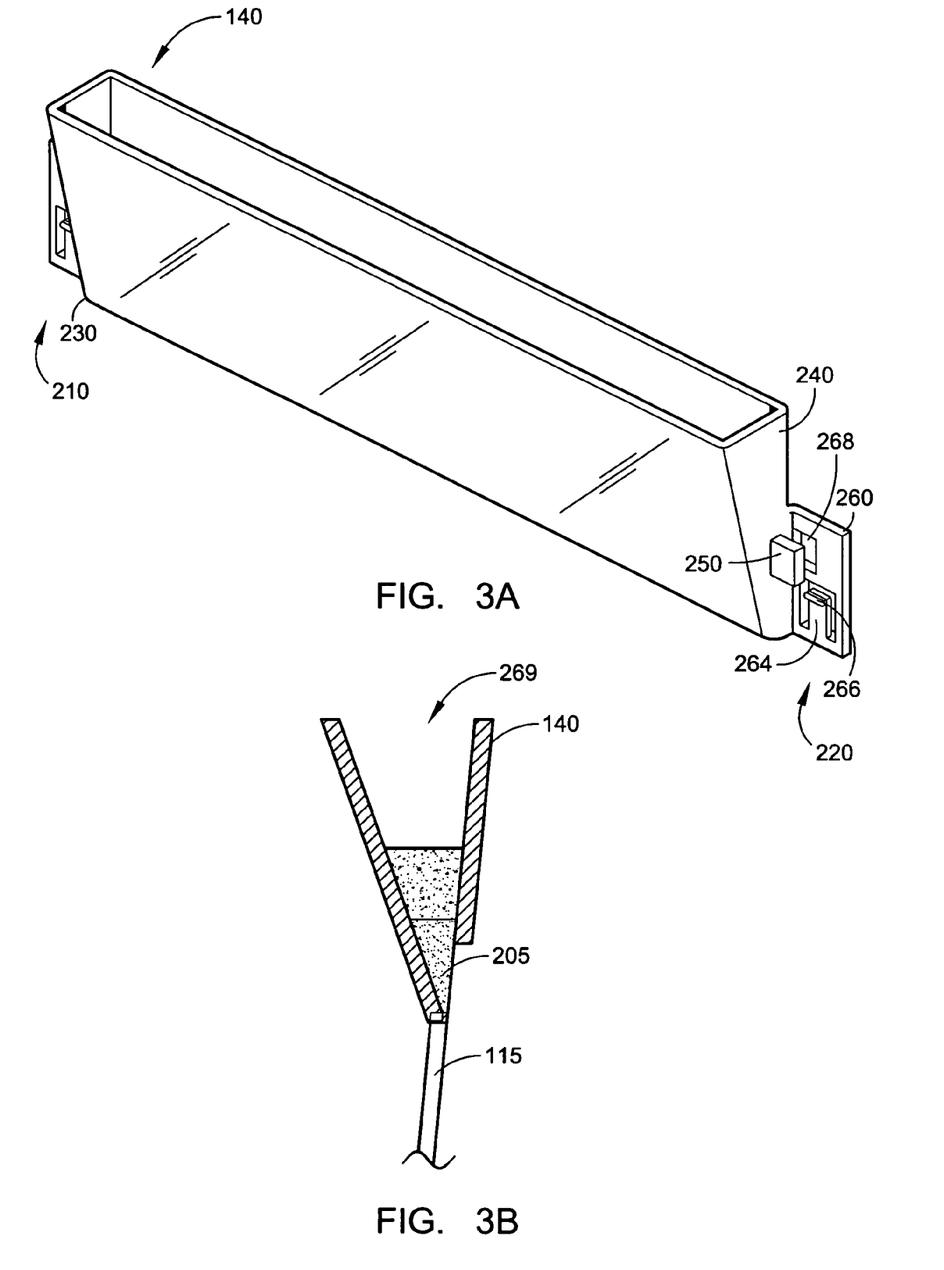
FIG. 3A is a perspective view of the "reservoir" used with the thin, plastic-film gel electrophoresis assembly illustrated in FIG. 1.
FIG. 3B is a cross-sectional view of the reservoir illustrated in FIG. 3A.

With reference additionally to FIGS. 2–3B, the reservoir 140 includes an upper portion 160, and intermediate portion 170, and a lower portion 180 that gradually tapers in thickness from a wide, open top 190, where samples are introduced, to a narrow, open bottom 200, where the samples electrophoretically migrate from a first stacking gel 205 in the reservoir 140 to the second resolving gel 115 sandwiched between the thin-film members 120, 130. The reservoir 140 has a trough-like configuration with a substantially wedge-shaped cross-section as shown in FIG. 3B. The lower portion 180 may include a plurality of divided wells and carries the stacking gel 205. The open bottom 200 of the lower portion has a thickness and a width substantially the same as the thickness and the width of the top of the resolving gel 115. At the open bottom 200, the bottom of the stacking gel 205 contacts the top of the resolving gel 115.

Mounting mechanisms 210, 220 extend from opposite ends 230, 240 of the reservoir 140. Each mounting mechanism 210, 220 includes a first, rectangular, small, front laterally protruding member 250 and a parallel second, rectangular, large, rear laterally protruding member 260. A flexible, resilient locking member 264 extends upward from a lower part of the rear laterally protruding member 260 and terminates in a forwardly protruding tang 266. A small rectangular window 268 is disposed in an upper part of the rear laterally protruding member 260. The mounting mechanisms 210, 220 ensure that the bottom of the stacking gel 205 is coplanar with, directly on top of, and in a fluid-tight seal with the resolving gel 115.

The stacking gel 205 fills the lower portion 180 of the reservoir 140, creating a liquid-tight seal with the upper surface of the resolving gel 115. The stacking gel 205 may extend below the bottom 200 of the reservoir 140 to make a butt joint with the resolving gel 115 when assembled. The stacking gel 205 is typically comprised of agarose, cross-linked polyacrylamide or a combination of agarose and polyacrylamide, where the polyacrylamide is polymerized using chemical-or photo-initiation techniques. The stacking gel 205 may include a buffer different from running buffers. The stacking gel 205 may also include denaturants and/or reducing agents. The upper portion 160, and/or intermediate portion 170, above the stacking gel 205, may include one of the running buffers. When employed for reducing application on proteins, an anti-oxidizing or reducing agent in the running buffer serves to maintain proteins in their fully denatured state by preventing the reformation of disulphide bonds. The first stacking gel may be a first dimension gel that has undergone isoelectric focusing. A binder solution may be used between the stacking gel 205 and the resolving gel 115 to maintain contact between the bottom of the stacking gel 205 and the top of the resolving gel 115. The binder solution may include 0.5% agarose and 0.5% linear polyacrylamide (600,000 to 1,000,000 Dalton molecular weight) in water. The binder solution may be applied during assembly of the thin, plastic-film gel electrophoresis assembly 100.

The upper part of the stacking gel 205 may be formed into one or more sample wells 269 by inserting a comb-shaped device into the reservoir 140 during polymerization of the stacking gel 205. The wells 269 may have various widths and depths, and may be formed along the entire thickness of the reservoir, or some portion of it. The wells 269 may be sufficiently wide and thick to accommodate a pipette for loading samples. As an example, in one embodiment of the present invention, for a one-dimensional electrophoresis gel assembly, the wells, 269 are 2 mm wide at the bottom, rise 10 mm with a 5 degree draft angle, and spaced 9 mm on center. The reservoir 140 may include thirteen wells 269. Twelve of the thirteen wells 269 may be used to run samples and the thirteenth well 269 may be used to run a molecular weight standard. In another embodiment, for one-dimensional preparative electrophoresis, the reservoir 140 may include a large, centered single well and gel strip, leaving 5 mm of the stacking gel on each side. Alternatively, in either of these two embodiments, solid plastic dividers in the reservoir 140 may be employed to divide the stacking gel 205 into the individual wells 269. In a third embodiment for two-dimensional electrophoresis, a small single well 269 is employed in the center and two wells 269 for the two first dimension buffers are provided near each end.

Figure 4:
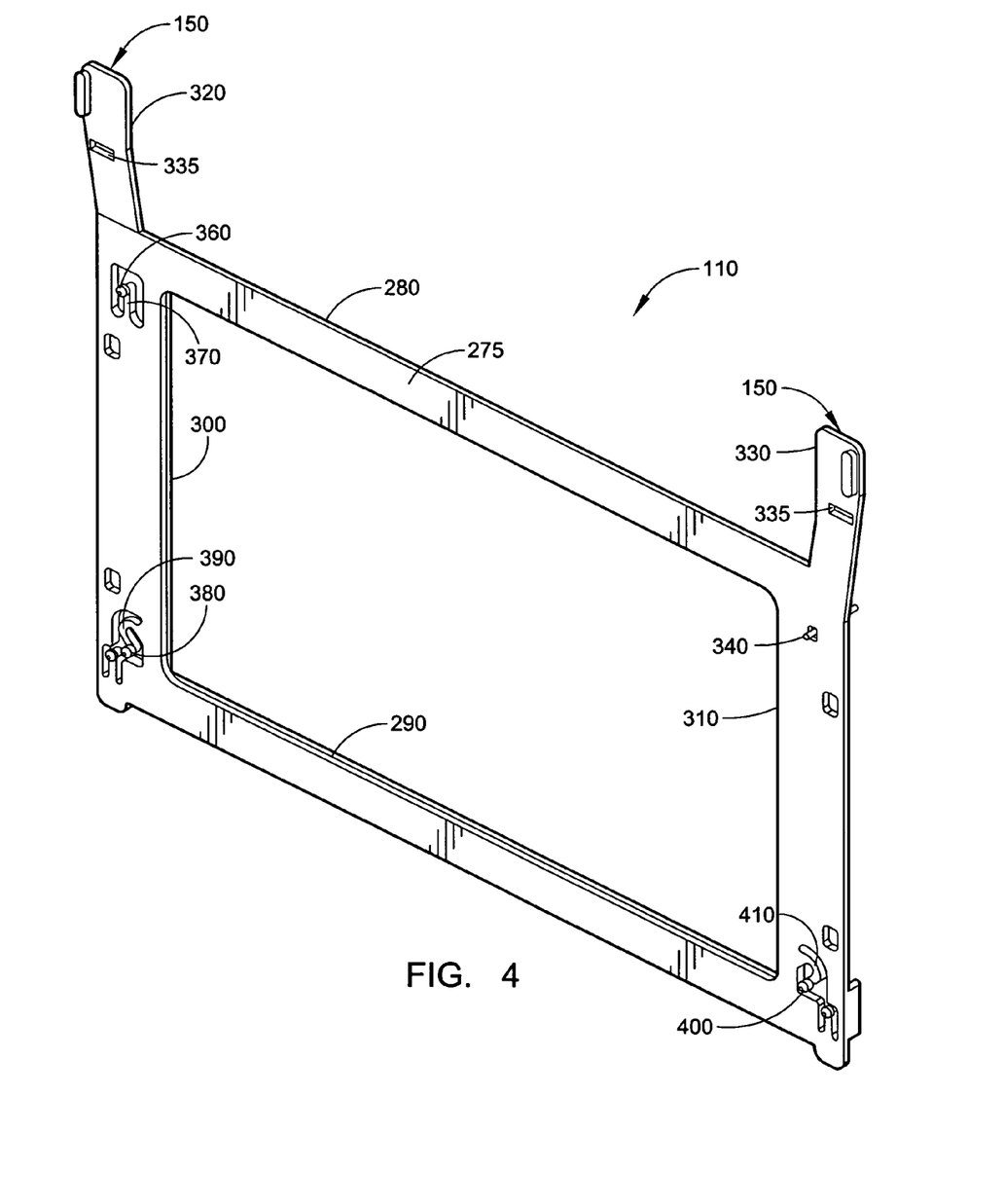
FIG. 4 is a perspective view of the support frame of the thin, plastic-film gel electrophoresis assembly illustrated in FIG. 1.

With reference additionally to FIG. 4, the support frame 110 will now be described in more detail. The support frame 110 is made of a flexible, resilient plastic material and has a substantially rectangular configuration with a central rectangular hole 270 and a substantially flat face 275. The support frame 110 includes an upper lateral support 280, a lower lateral support 290, a left vertical support 300, and a right vertical support 310. The vertical supports 300, 310 terminate at their tops 150 in ear-like, flat protrusions 320, 330. The flat protrusions 320, 330 include narrow, laterally elongated, rectangular holes 335.

Figure 5:
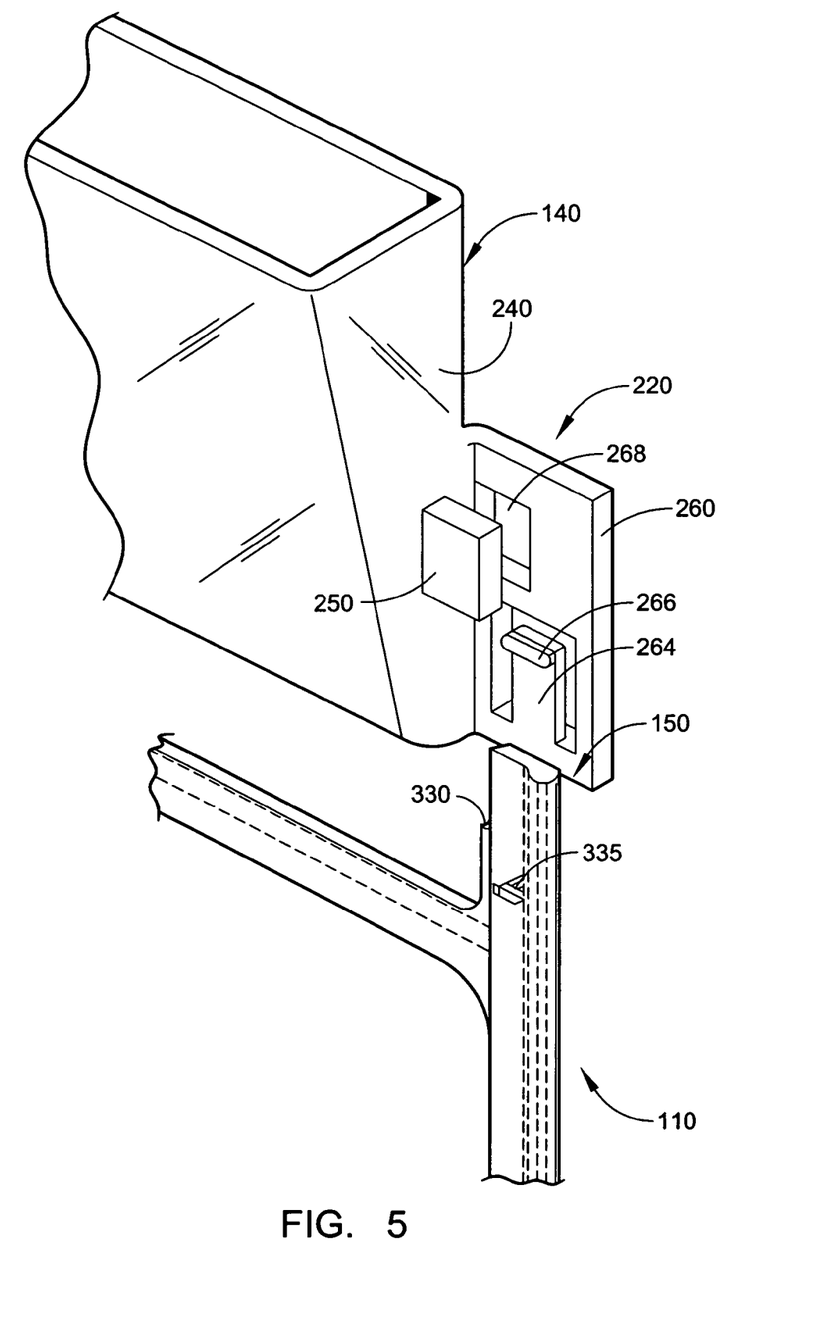
FIG. 5 is a partial perspective view of the reservoir and the support frame of the thin, plastic-film gel electrophoresis assembly illustrated in FIG. 1.

With reference additionally to FIG. 5, to mount the reservoir 140 to the support frame 110, the ear-like, flat protrusions 320, 330 are slid between the front and rear protruding members 250, 260 of the mounting mechanisms 210, 220. This sliding causes the flexible, resilient locking members 264 to be urged rearward. The resilient locking members 264 provide a biasing force in a direction opposite to that in which the resilient locking members 264 are displaced. Once the protruding tangs 266 of the locking members 264 are over the narrow, laterally elongated, rectangular holes 335, the resilient locking members 264 urge the tangs 266 into the holes 335, locking the reservoir 140 in place with respect to the rest of the electrophoresis assembly 100.

With reference back to FIG. 4, a fixed support post 340 extends outwardly from the right vertical support 310 near an upper-right corner of the support frame 110. The support post 340 includes an undercut on a right portion of the support post 340.

A support post 360 extends outwardly from the left vertical support 300 near an upper-left corner of the support frame 110. The support post 360 is connected to the left vertical support 300 via a flexible, resilient, straight connection member 370. Similar to a spring, the connection member 370 provides a biasing force in a direction opposite to that in which it is displaced. The connection member 370 may be moved laterally, forward, and rearward. The support post 360 includes an undercut similar to the undercut described above with respect to the fixed support post 340, but the undercut extends around the entire circumference of the support post 360, except where the support post 360 is attached to the connection member 370.

A support post 380 extends outwardly from the left vertical support 300 near a lower-left corner of the support frame 110. The support post 380 is connected to the left vertical support 300 via a flexible, resilient, curved, hook-shaped connection member 390. Similar to a spring, the connection member 390 provides a biasing force in a direction opposite to that in which it is displaced. The connection member 390 may be moved up and to the right, down and to the left, forward, and rearward. Because the connection member 390 is curved, if the connection member 390 is displaced, for example, upward and toward the right, the connection member 390 will provide a biasing force in an opposite direction, namely, downward and toward the left. The support post 380 includes an undercut similar to the undercut described above with respect to the fixed support post 340, but the undercut extends around a lower-left portion of the circumference of the support post 380.

A support post 400 extends outwardly from the right vertical support 310 near a lower-right corner of the support frame 110. The support post 400 is connected to the right vertical support 310 via a flexible, resilient, curved, hook-shaped connection member 410, similar to the connection member 390. If the connection member 410 is displaced, for example, upward and toward the left, the connection member 410 will provide a biasing force in an opposite direction, namely, downward and toward the right. The connection member 410 may be moved up and to the left, down and to the right, forward, and rearward. The support post 400 includes an undercut similar to the undercut described above with respect to the fixed support post 340, but the undercut extends around a lower-right portion of the circumference of the support post 380.

With reference back to FIG. 2, the resolving gel 115 is carried by the support frame 110, sandwiched between the inner thin-film member 120 and outer thin-film member 130. The resolving gel 115 includes a suitable matrix for separating bio-molecules, water and buffer constituents. By way of example, suitable matrices include cross-linked polyacrylamide, with or without substitution, agarose, derived agarose or other polysaccharides, starch or other materials. The preferred materials are polymerized acrylamide 6 to 20% with N,N'-methylene-bis-acrylamide ("Bis") as a crosslinker in the range of 1 to 5% of total monomer, or a similar polymer made from N-methyl-acrylamide and Bis. The most preferred matrix is cross-linked polyacrylamide, in the range of 6 to 20%, with agarose in the range of 0.2 to 1.0%.

Polymerization of acrylamide compounds may be effected by usual means, including chemical methods (e.g., ammonium persulfate (APS) and N,N,N',N'-tetra-ethyl-methylene-diamine (TEMED), photo-initiated polymerization methods (e.g., riboflavin with APS and TEMED, or methylene blue with sodium toluene-sulfinate and diphenyliodinium chloride [see Lyubimova, et al., "Polymerization of Polyacrylamide Gels with Methylene Blue," *Electrophoresis*, 14 (1993) 40–50]), or other methods. Photo-initiation is the preferred method of acrylamide polymerization when agarose is included.

The resolving gel 115 may include a buffer different from running buffers. The buffer may include any substance useful for electrophoresis, such as described in the work by Jovin ("Multiphasic Zone Electrophoresis," Biochemistry 12[5] (1973) 871–898) for stacking systems or continuous buffer systems such as tris-hydroxy-methyl-amino-methane (Tris). The buffer may include 0.375 M Tris/chloride at pH 8.6 to 8.8 (see Laemmli, Nature, 227 (1970) 680–686), 0.9 M Tris/chloride at pH 8.45 (see Schaegger et al., Analytical Biochemistry, 166 (1987) 368–379), bis.-(2-hydroxyethyl)-imino-tris-15 (hydroxymethyl)-methane ("BisTris")/chloride (see Moos, et al., J. Biological Chemistry, 263 [131 (1988) 6005–6008, and Engelhom et al., U.S. Pat. No. 5,578,180). Detergents such as sodium dodecyl-sulphate (SDS) may be employed in the resolving gel 115 as well. Other buffer materials are Tris/borate/ethylene-dieimine-tetra-acetic acid (EDTA) and BisTris/N-tris-(hydroxymethyl)-methyl-glycine ("Tricine")/EDTA (see Updyke, et al., U.S. Pat. No. 5,922,185) with or without denaturants such as urea or formamide.

The thin-film members 120, 130 are generally rectangular and preferably have a thickness ranging from approximately 0.002 in. to approximately 0.020 in. In a preferred embodiment, the thin-film members 120, 130 are substantially 0.004 in. thick. Low oxygen permeable materials such as cellophane film, polyester film, polyvinylidene chloride (PVDC)-coated plastic film, especially polyamide films such as Nylon, or plastic films coated with a high-density silica-layer are suitable. Additional details of each of the thin-film members 120 will now be described.

Figure 6:
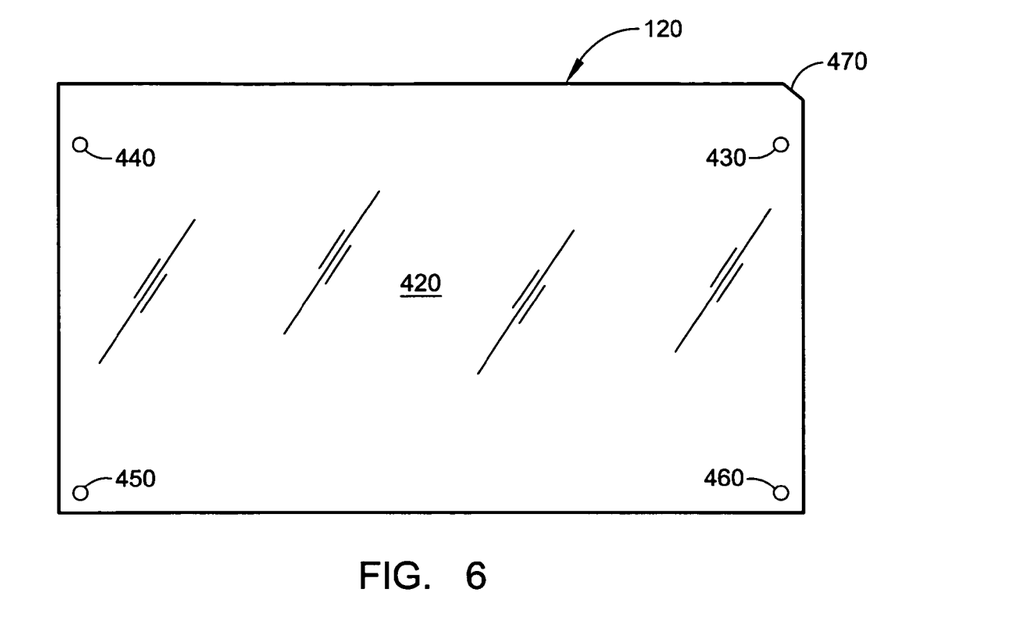
FIG. 6 is a top plan view of a first, inner thin-film member.

With reference additionally to FIG. 6, the inner-thin-film member 120 may include the resolving gel 115 on a front side 420. The inner thin-film member 120 includes four holes 430, 440, 450, 460 that receive the four support posts 340, 360, 380, 400 in a manner to be described. The holes 430, 440, 450, 460 are located near the corners of the inner thin-film member 120, outside of where the electrophoretic separation occurs. A small, upper-right hole 430 is circular. An upper-left hole 440 is laterally elongated to allow for lateral movement of the upper-left support post 360 therein. A lower-left hole 450 has a round, diamond shape and is larger than the upper-right hole 430. A lower-right hole 460 is similar in shape and size to the lower-left hole 450. A clipped corner 470 of the inner thin-film member 120 may help in orienting the inner thin-film member 120 when mounting it to the support frame 110.

Figure 7:
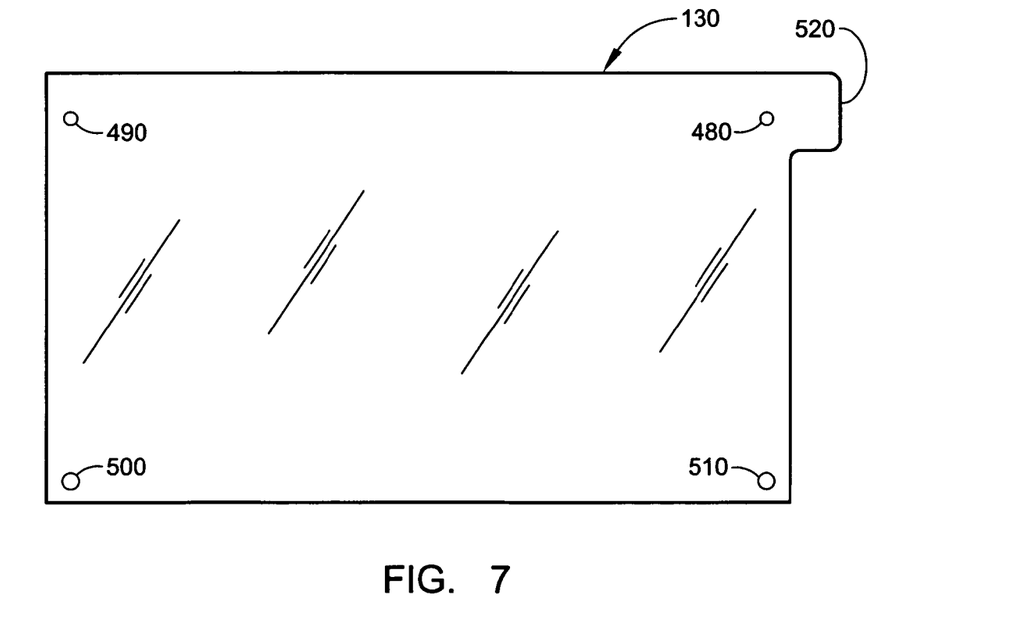
FIG. 7 is a top plan view of a second, outer thin-film member.

With reference additionally to FIG. 7, the outer thin-film member 130 will now be described. The outer thin-film member 130 is disposed on the resolving gel 115, on an opposite side of the gel 115 from the inner thin-film member 120. The outer thin-film member 130 includes four holes 480, 490, 500, 510 that receive the four support posts 340, 360, 380, 400 in a manner to be described. The holes 480, 490, 500, 510 are located near the corners of the outer thin-film member 130, outside of where the electrophoretic separation occurs. A small, upper-right hole 480 and upper-left hole 490 are circular. A lower-left hole 500 and a lower-right hole, 510 have round, diamond shapes and are larger than the upper holes 480, 490. The left holes 490, 500 are closer to the right holes 480, 510 than the corresponding holes, in the outer thin-film member 130. A tabbed corner 520 of the outer thin-film member 130 may be used to handle the outer thin-film member 130 and may help orient the outer thin-film member 130 when mounting it to the support frame 110. Although the holes 430–460, 480–510 have been described as having a certain configuration and being a certain number, in alternative embodiments, the configuration of one or more of the holes and the number of holes may be different.

The gel electrophoresis system 100 may include an anti-shifting mechanism to prevent the resolving gel 115 from slipping, shifting or moving relative to the system 100. The anti-shifting mechanism may include clamps or pins. In a preferred embodiment, the anti-shifting mechanism is an adhesive layer on either or both of the inner surfaces of the thin-film members 120, 130. An exemplary adhesive layer that may be used as an anti-shifting mechanism for acrylamide gels is described in U.S. Pat. No. 4,415,428 to Nochumson, which is incorporated by reference as though set forth in full. Another exemplary adhesive layer that may be used as an anti-shifting mechanism for agarose gels or acrylamide/agarose composites is an agarose coating sold under the name Gel Fix for Agarose by Serva Electrophoresis GmbH of Heidelberg, Germany. A further exemplary adhesive layer that may be used as an anti-shifting mechanism is described in U.S. Pat. No. 4,737,259 to Ogawa; this adhesive layer is a porous, low-density silica layer that causes physical entrapment of a gel formed on its surface.

With reference to FIGS. 1–7, a method of assembling the thin, plastic-film gel electrophoresis assembly 100 will now be described. The first stacking gel 205 and the second resolving gel 115 are cast separately in any well-known manner in the art. As indicated above, the inner thin-film member 120 may be cut into sheets with the configuration shown in FIG. 6 and may include the second resolving gel 115 on the front side 420, laterally centered between the left holes 440, 450 and the right holes 430, 460. The inner thin-film member 120 is attached to the support frame 110 via the posts 340, 360, 380, 400 and the holes 430, 440, 450, 460. The clipped corner 470 may be used to properly orient the inner thin-film member 120 when attaching it to the support frame 110. The inner thin-film member 120 is preferably applied to the support frame 110 by aligning and placing the holes 430, 440, 450, 460 over the posts 340, 360, 380, 400 one at a time. The rims that define the holes 430, 440, 450, 460 catch on the undercuts of the posts 340, 360, 380, 400, helping to secure the inner thin-film member 120 to the posts 340, 360, 380, 400. The support frame 110 may be flexed and/or the connecting members 370, 390, 410 may be flexed (which may include pushing the connecting members 370, 390, 410 and posts 360, 380, 400 towards the user from behind the support frame 110) to assist in hole alignment and placement over the posts 340, 360, 380, 400. When the support frame 110 and/or connecting members 370, 390, 410 are released, tension in the connection members 370, 390, 410 causes the inner thin-film member 120 to be stretched tightly and securely across the support frame 110.

In a similar manner, the holes 480, 490, 500, 510 of the outer thin-film member 130 may be applied to the posts 340, 360, 380, 400 of the support frame 110, securing the resolving gel 115 to the support frame 110. The outer thin-film member 130 may be handled using the tabbed corner 520, which also indicates the proper orientation of the outer thin-film member 130. Because the left holes 490, 500 are closer to the right holes 480, 510 than the corresponding holes of the inner thin-film member 120, application of the outer thin-film member 130 causes the connection members 370, 390, 410 to flex more than application of the inner thin-film member 120. The holes 440, 450, 460 of the inner thin-film member 120 are sized to accommodate the movement of the support posts 360, 380, 400 caused by this greater flexing of the connection members 370, 390, 410 during application of the outer thin-film member 130. The flexing of the upper-left connection member 370 causes, the support post 360 to pull the upper-left corner of the outer thin-film member 130 to the left. The flexing of the lower-left connection member 390 causes the support post 3813 to pull the lower-left corner of the outer thin-film member 130 to the left and downward. The flexing of the lower-right connection member 410 causes the support post 400 to pull the lower-right corner of the outer thin-film member 130 to the right and downward. The cumulative effect of the pulling of the connection members 370, 390, 410 puts the outer thin-film member 130 in more tension than the inner thin-film member 120, maintaining a constant space between the thin-film members 120, 130, eliminating distortion problems caused by the gel having a non-uniform thickness or non-uniform heating. When the outer thin-film member 130 and inner thin-film member 120 mounted to the support frame 110, the second resolving gel 115 is exposed (not sealed) on its perimeter.

With reference to FIG. 5, the separately cast first stacking gel 215 and second resolving gel 115 are then brought together by mounting the reservoir 140 onto the support frame 110. To mount the reservoir 140 to the support frame 110, the ear-like, flat protrusions 320, 330 are slid between the front and rear protruding members 250, 260 of the mounting mechanisms 210, 220. During this sliding process, the rear of the reservoir 140 is slid over the top of the front of the inner thin-film member. As the protrusions 320, 330 are slid between the protruding members 250, 260, the flexible, resilient locking members 264 are urged rearward. This causes the resilient locking members 264 to provide a biasing force in a direction opposite to that in which the resilient locking members 264 are displaced. Once the protruding tangs 266 of the locking members 264 are over the narrow rectangular holes 335, the resilient locking members 264 urge the tangs 266 into the holes 335, locking the reservoir 140 in place with respect to the rest of the electrophoresis assembly 100. In this position, the lower surface of the stacking gel 205 forms a liquid tight seal with the upper surface of the resolving gel 115. As mentioned above, prior to bringing the stacking gel 205 in contact with the resolving gel 115, a binder solution may be applied to the upper surface of the resolving gel 115 and/or lower surface of the stacking gel 205 to maintain contact between the gels 115, 205. When the stacking gel 205 is in contact with the resolving gel 115, the resolving gel 115 is exposed (not sealed) on the remainder of its perimeter.

The top of the stacking gel 205 and the bottom of the resolving gel 115 are placed in contact with buffer solutions which make electrical contact between the gels and the cathode or anode of an electrical power supply.

A sample containing macromolecules and a tracking dye may be placed on top of the upper gel. An electric potential is applied, causing the sample macromolecules and tracking dye to migrate toward the bottom of the lower gel. The locations of the bands of separated macromolecules are then determined. By comparing the distance moved by particular bands in comparison to the tracking dye and macromolecules of known mobility, the mobility of sample macromolecules can be determined. Once the mobility of the sample macromolecules is determined, the size of the macromolecule can be calculated.

With reference to FIGS. 8–11, a thin, plastic-film gel electrophoresis assembly 600 constructed in accordance with an alternative embodiment of the invention will now be described. The electrophoresis assembly 600 is the same as the electrophoresis assembly 100 described above, except for the specific features described below. One or more of the features described with respect to the electrophoresis assembly 600 may be incorporated into the electrophoresis assembly 100 and vice versa.

Figure 8:
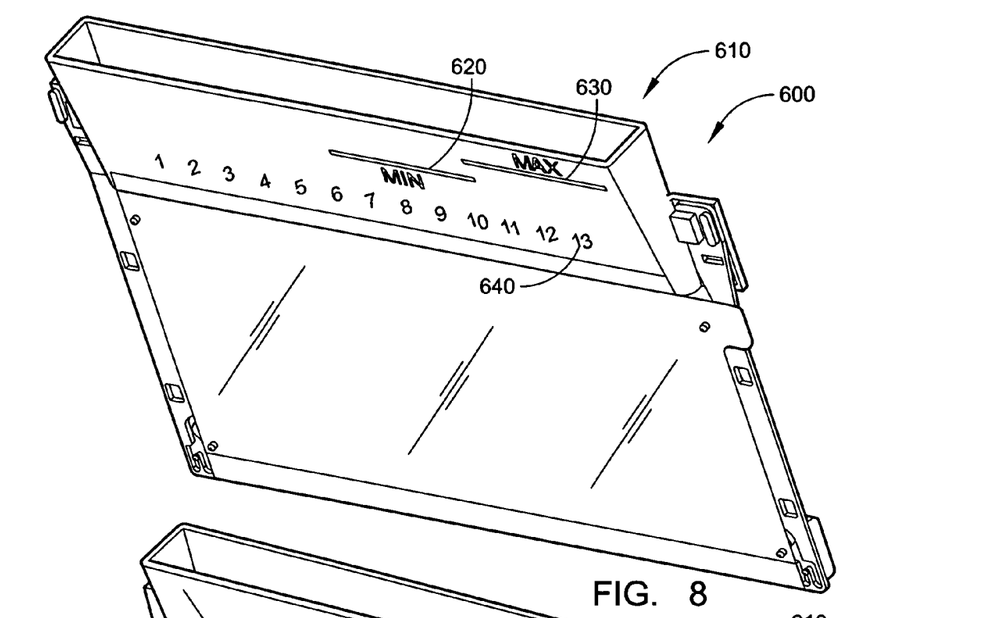
FIG. 8 is a perspective view of an alternative embodiment of a thin, plastic-film gel electrophoresis assembly.
Figure 9:
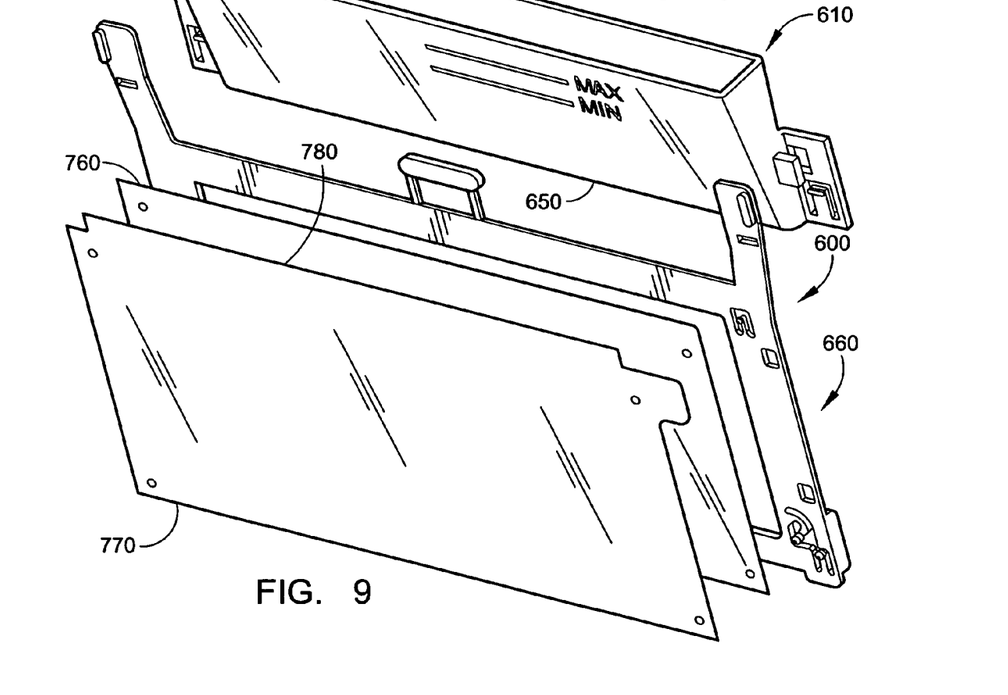
FIG. 9 is an exploded perspective view of the thin, plastic-film gel electrophoresis assembly illustrated in FIG. 8.

The electrophoresis assembly 600 includes a reservoir 610 with a minimum fill line 620 and a maximum fill line 630 for indicating the minimum volume height and maximum volume height for maintaining the proper solution volume (e.g., running buffer) in the reservoir 610. The running buffer should have a concentration sufficient to provide an excess of ions as compared to those in the gel assembly and should have a density below that of the samples so that the samples remain at the bottom of the well(s). Further, the locations of the wells of the reservoir 610 may be indicated with numbers 640. The reservoir 610 includes an open bottom 650 with a draft angle of 5 degrees. One must not have too large of an angle across the stacking gel to get sharp bands in the upper portion of the separating gel. In a preferred embodiment, the draft angle is 15 degrees or less. In a more preferred embodiment, the draft angle is 10 degrees or less. In a most preferred embodiment, the draft angle is 5 degrees. The reservoir 610 also preferably has a step-shaped cross-sectional configuration.

Figure 10:
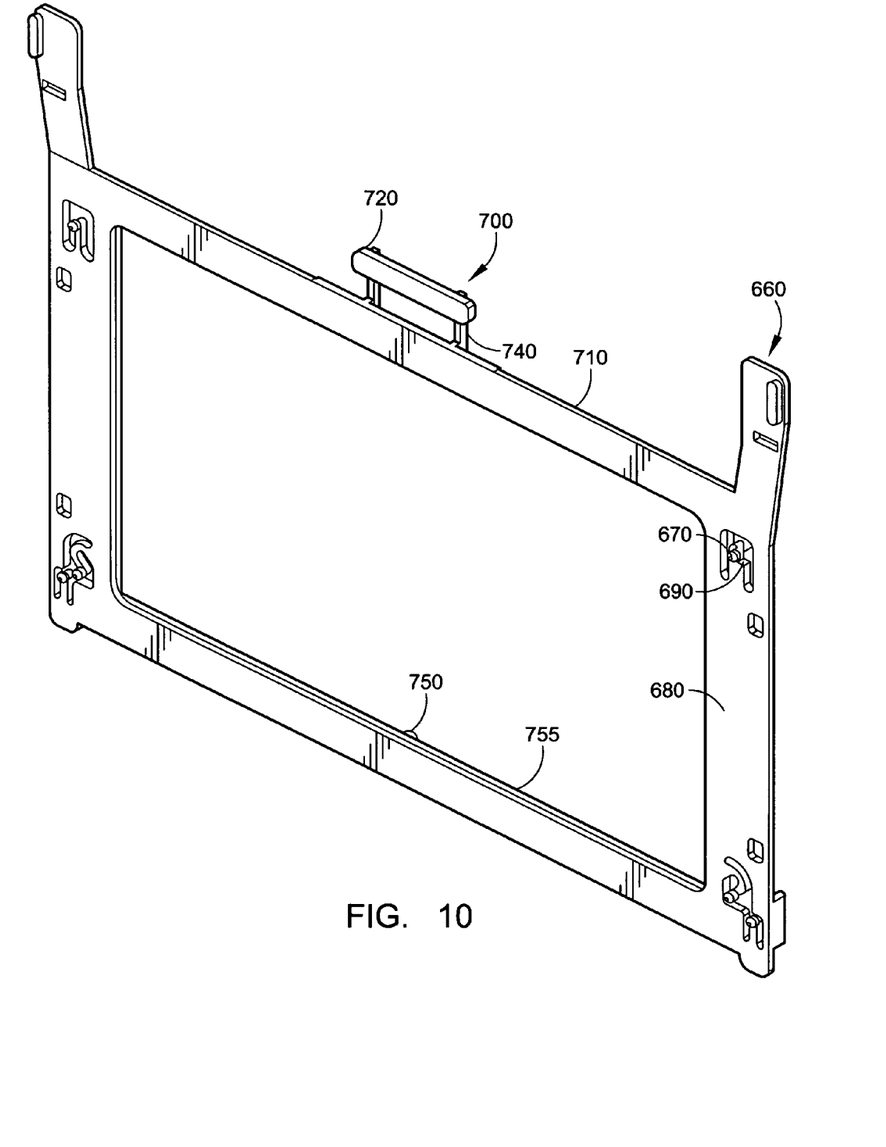
FIG. 10 is a front perspective view of the support frame of the thin, plastic-film gel electrophoresis assembly illustrated in FIG. 8.

With reference to FIG. 10, a support frame 660 of the electrophoresis assembly 600 includes a support post 670 connected to a right vertical support 680 via a flexible, resilient, step-shaped connection member 690 instead of the fixed support post 340. The support post 670 extends outwardly from the right vertical support 680 near an upper-right corner of the support frame 660. Similar to a spring, the connection member 690 provides a biasing force in a direction opposite to that in which it is displaced. The connection member 690 may be moved laterally, forward, and rearward. The support post 670 may include an undercut similar to the undercut described above with respect to the fixed support post 340.

A central support 700 extends from a rear side of an upper lateral support 710 to ensure that the center of the reservoir 610 maintains its planar relationship to the support frame 660. When the reservoir 610 is mounted to the top of the support frame 660, the central support 700 may urge the central part of the reservoir 610 forward so that the central portion of the reservoir 610 maintains its planar relationship to the support frame 660. The central support 700 includes a rail 720 with a flat front face 730. The rail 720 is connected to a rear side of the upper lateral support 710 through vertical, flexible, resilient connection members 740. Similar to a spring, the connection members 740 provide a biasing force in a direction opposite to that in which they are displaced. In alternative embodiments, the central support 700 may take alternative configurations. For example, but not by way of limitation, the central support 700 may slide into a pair of L-shaped connection members of the reservoir 610.

Figure 11:
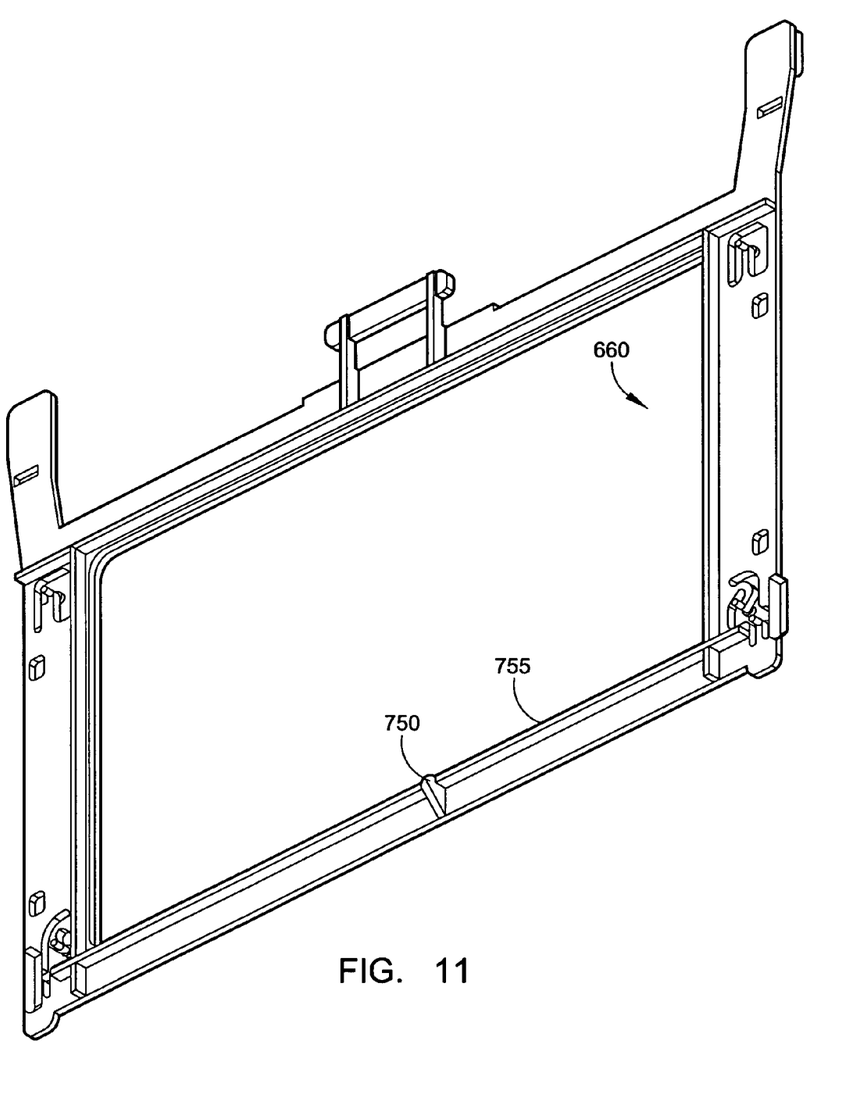
FIG. 11 is a front perspective view of the support frame of the thin, plastic-film gel electrophoresis assembly illustrated in FIG. 8.

With reference to FIGS. 10 and 11, an inclined cam member 750 on the rear face of the lower lateral support 290 may be used to urge the central portion of a lower lateral support 755 forward when the support frame 660 is dropped into a lower buffer assembly or support structure. When the support frame 660 is lowered into the lower support structure, a wall (not shown) of the lower support structure abuts the inclined cam member 750, causing the central portion of the lower lateral support 290 to be urged forward. This is important because the support frame 660 is preferably made of a resilient material that may bend slightly in the central portion by the pulling of thin-film members 760, 770 on opposite sides of the support frame 660. The inclined cam member 750 inhibits this bending and helps maintain parallel, uniform spacing between the thin-film members 760, 770. Maintaining a constant space between the thin-film members 760, 770 eliminates distortion problems caused by the gel having a non-uniform thickness or non-uniform heating.

An outer thin-film member 770 may include an additional top extender or additional height 780 so that when the reservoir 610 is mounted to the top of the resolving gel and the thin-film members 760, 770, the top extender 780 extends to a height that prevents the resolving gel from being exposed on the front of the electrophoresis assembly 600. Exposure of the resolving gel on the front of the electrophoresis assembly 600 is important for preventing evaporative loss of water and subsequent collapse of the gel and loss of contact between the stacking gel and the resolving gel.

This invention offers several improvements to the prior art, some of which are described below. In general, this invention provides for low cost manufacturing of pre-cast electrophoresis gel assemblies cast between films, which contains a separate first gel for stacking, and can easily be run vertically. The cost associated with making a flat slab gel assemblies is a part of the process, rather than incorporated into every gel assembly. Moreover, this invention permits the first gel to be formed at some earlier time to its use and to have not only a different polymer concentration, but also distinct buffer species for improved stacking or additional components such as a reducing agent for improved homogeneity of sample components. Finally, this invention permits two-dimensional applications to be performed using a first-dimension gel in the reservoir run laterally followed by joining the result to the second gel and performing the second-dimension separation vertically.

Because the reservoir provides a liquid tight seal, there is no need for a rigid and sealed second gel structure to seal the buffers in a running chamber to the gel assembly for running vertically. Further, because there is no requirement for a sealed gel cassette, the gel can be cast inexpensively in a continuous horizontal process. Furthermore, since the first and second gels are cast in two parts, even horizontally cast homogeneous second gels still have a lower percentage first gel for stacking resulting in improved band sharpness. Because the two gels do not need to be in contact until they are ready to run and small molecules cannot diffuse between them, it is possible to have different buffers or additives in the first gel and second gel for sharper bands. Moreover, as the two gels are not in contact until they are ready to run and small molecules cannot diffuse between them, it is possible to have a two-dimensional system where a first dimension separation takes place in the first gel with the reservoir alone, and a second dimension separation takes place when the completed first dimension gel is placed in contact with the second gel. Also, because the supporting structure can be coated with different binding and release layers, gels can be cast inexpensively in a batch vertical process.

It will be readily apparent to those skilled in the art that still further changes and modifications in the actual concepts described herein can readily be made without departing from the spirit and scope of the invention as defined by the following claims.

What is claimed is:

1. A thin-film, electrophoresis assembly, comprising: a support frame including a top portion and a substantially flat face; a first thin-film member carried by the support frame; a second thin-film member carried by the support frame; a resolving gel sandwiched between the first thin-film member and the second thin-film member, the resolving gel including a top surface; a reservoir mounted to the top portion of the support frame, the reservoir including an open top and an open bottom; and a stacking gel carried by the reservoir and including a bottom surface in fluid-tight communication with the top surface of the resolving gel through the open bottom of the reservoir.

2. The electrophoresis assembly of claim 1, wherein the thin-film members have a thickness between 0.002 in. and 0.02 in.

3. The electrophoresis assembly of claim 1, wherein the thin-film members have a thickness of substantially 0.004 in.

4. The electrophoresis assembly of claim 1, wherein the electrophoresis assembly includes one or more mounting mechanisms to mount the reservoir to the top portion of the support frame.

5. The electrophoresis assembly of claim 1, wherein the support frame includes ear-like, flat protrusions that extend upwardly from the top portion of the support frame, the reservoir includes front and rear protruding members that extend outward and laterally from the reservoir, and the ear-like, flat protrusions are slidably received by the front and rear protruding members to mount the reservoir to the support frame.

6. The electrophoresis assembly of claim 5, wherein the rear protruding members include flexible, resilient locking members terminating in tangs, the ear-like, flat protrusions of the support frame include holes that receive the tangs of the resilient locking members to lock the reservoir in position relative to the support frame.

7. The electrophoresis assembly of claim 1, wherein the reservoir includes a trough-like configuration.

8. The electrophoresis assembly of claim 7, wherein the reservoir decreases in thickness from the open top to the open bottom.

9. The electrophoresis assembly of claim 1, wherein the support frame is a substantially rectangular support frame having an interconnected upper lateral support, a lower lateral support, a left vertical support, and a right vertical support, and the first thin-film member and the second thin-film member are substantially rectangular.

10. The electrophoresis assembly of claim 1, further including an adhesive layer between the resolving layer and at least one of the-first thin-film member and the second thin-film member.

* * * * *